(12) United States Patent
Takebayashi et al.

(10) Patent No.: US 9,855,542 B2
(45) Date of Patent: Jan. 2, 2018

(54) SUBSTRATE FOR BIOCHIPS AND METHOD FOR PRODUCING SAME

(71) Applicant: Nippon Light Metal Company, Ltd., Tokyo (JP)

(72) Inventors: Yasushi Takebayashi, Shizuoka (JP); Ryo Morishita, Shizuoka (JP); Kei Yamaguchi, Shizuoka (JP)

(73) Assignee: NIPPON LIGHT METAL COMPANY, LTD., Tokyo (JP)

( * ) Notice: Subject to any disclaimer, the term of this patent is extended or adjusted under 35 U.S.C. 154(b) by 0 days.

(21) Appl. No.: 14/759,793

(22) PCT Filed: Jan. 7, 2014

(86) PCT No.: PCT/JP2014/050071
§ 371 (c)(1),
(2) Date: Jul. 8, 2015

(87) PCT Pub. No.: WO2014/109312
PCT Pub. Date: Jul. 17, 2014

(65) Prior Publication Data
US 2015/0352511 A1 Dec. 10, 2015

(30) Foreign Application Priority Data

Jan. 9, 2013 (JP) .................................. 2013-001497

(51) Int. Cl.
| | |
|---|---|
| *B01J 19/12* | (2006.01) |
| *B01J 19/00* | (2006.01) |
| *G01N 33/543* | (2006.01) |
| *C12Q 1/68* | (2006.01) |
| *B01L 3/00* | (2006.01) |

(52) U.S. Cl.
CPC ..... *B01J 19/0046* (2013.01); *B01L 3/502707* (2013.01); *C12Q 1/6876* (2013.01); *G01N 33/54366* (2013.01); *G01N 33/54393* (2013.01); *B01J 2219/00527* (2013.01); *B01J 2219/00529* (2013.01); *C12Q 1/6837* (2013.01)

(58) Field of Classification Search
CPC .......... B01J 19/0046; B01J 2219/00527; B01J 2219/00529; B01L 3/502707
See application file for complete search history.

(56) References Cited

U.S. PATENT DOCUMENTS

| | | | |
|---|---|---|---|
| 8,822,607 B2* | 9/2014 | Nokihara | ............. C12Q 1/6837 427/249.6 |
| 9,164,082 B2* | 10/2015 | Inoue | ..................... G01N 21/01 |
| 2002/0197417 A1 | 12/2002 | Nakamura et al. | |
| 2010/0184622 A1 | 7/2010 | Nokihara et al. | |
| 2011/0111531 A1 | 5/2011 | Yamano et al. | |
| 2011/0152409 A1* | 6/2011 | Nokihara | ............. C12Q 1/6837 524/27 |
| 2012/0088690 A1 | 4/2012 | Hirayama et al. | |
| 2014/0220316 A1* | 8/2014 | Inoue | ..................... G01N 21/01 428/201 |

FOREIGN PATENT DOCUMENTS

| | | | | |
|---|---|---|---|---|
| JP | 2002-350440 A | | 12/2002 | |
| JP | 2006-308307 A | | 11/2006 | |
| JP | 2006-322708 A | | 11/2006 | |
| JP | 2006-329686 A | | 12/2006 | |
| JP | 2008-249416 A | | 10/2008 | |
| JP | 2010-008378 A | | 1/2010 | |
| JP | 2010-014620 A | | 1/2010 | |
| JP | 2010014620 A | * | 1/2010 | |
| WO | WO 0102538 A1 | * | 1/2001 | ......... C03C 17/3405 |
| WO | WO 02/052045 A1 | | 7/2002 | |
| WO | WO 2005/001121 A1 | | 1/2005 | |
| WO | WO 2013027777 A1 | * | 2/2013 | ............. G01N 21/01 |

OTHER PUBLICATIONS

Extended European Search Report dated Jul. 11, 2016, for European Application No. 14737520.8.
International Search Report issued in PCT/JP2014/050071, dated Apr. 15, 2014.

* cited by examiner

*Primary Examiner* — Nicholas Hill
(74) *Attorney, Agent, or Firm* — Birch, Stewart, Kolasch & Birch, LLP

(57) ABSTRACT

A substrate for biochips, in which carboxyl groups are immobilized on a substrate whose surface at least is composed of carbon; and a method for producing the substrate are disclosed. The substrate for biochips comprises a substrate whose surface at least is composed of carbon; and an acrylic polymer having free carboxyl groups in the molecular structure thereof, which acrylic polymer is immobilized on the surface of the substrate. The method for producing the substrate comprises irradiating the substrate whose surface at least is composed of carbon with ultraviolet light during the acrylic polymer having free carboxyl groups in the molecular structure thereof contacts the substrate.

4 Claims, No Drawings

SUBSTRATE FOR BIOCHIPS AND METHOD FOR PRODUCING SAME

TECHNICAL FIELD

The present invention relates to a substrate for biochips which has free carboxyl groups on the surface of the substrate, and a method for producing the same.

BACKGROUND ART

Biochips such as a protein chip, peptide chip and DNA chip are widely used for diagnosis and research of various diseases. The biochips which have been widely used are usually obtained by immobilizing biologically relevant substances such as a protein, peptide and DNA on a glass substrate such as a slide glass.

However, the conventional biochips using the glass substrate were likely to cause non-specific adsorption and had a problem in accuracy of measurement. Also, since the glass substrate induces autofluorescence, measurements employing fluorescent labels which have been often used recently, had a problem in accuracy.

In order to solve these problems, a substrate for biochips, in which a carbon-containing layer having an active group(s) is formed on a metal substrate, and a biologically relevant substance(s) is/are bound to the active group(s), is provided (Patent Document 1). This substrate for biochips has excellent properties that autofluorescence is not induced, a biologically relevant substance(s) can be immobilized easily, processing of the substrate is easy, and high flatness and surface precision can be attained. Also, carboxyl group is exemplified as the active group. However, as a method employing carboxyl group as the active group, only the method in which amino groups are first bound to a carbon-containing layer, and then the amino groups are converted to diazonium ions, the diazonium ions are converted to nitriles, and the resulting nitriles are hydrolyzed, is disclosed, and the method is not concretely described.

Further, a substrate for biochips, in which an amino group-containing polymer is covalently bound on the substrate whose surface at least is composed of carbon, is also provided (Patent Document 2). The biologically relevant substance(s) is(are) covalently bound to the amino groups.

PRIOR ART DOCUMENTS

Patent Document

Patent Document 1: JP 2006-329686 A
Patent Document 2: JP 2010-008378 A

SUMMARY OF THE INVENTION

Problems to be Solved by the Invention

The biologically relevant substances which do not bind to amino groups exist, and biochips having carboxyl groups bound to the surface of the substrate thereof are demanded. However, biochips having carboxyl groups suitably bound on the substrate whose surface at least is composed of carbon do not exist.

Therefore, an object of the present invention is to provide a substrate for biochips, in which carboxyl groups are immobilized on the substrate whose surface at least is composed of carbon; and a method for producing the same.

Means for Solving the Problems

The present inventors intensively studied to confirm experimentally that an acrylic polymer can be immobilized on carbon and carboxyl groups of the acrylic polymer can be exposed in the free state on the surface of the substrate by irradiation with ultraviolet light during the acrylic polymer contacts the carbon constituting the surface of the substrate, and further that biologically relevant substances can be bound to the carboxyl groups, thereby completing the present invention.

That is, the present invention provides a substrate for biochips, the substrate comprising a substrate whose surface at least is composed of carbon; and an acrylic polymer having free carboxyl groups in the molecular structure thereof, which acrylic polymer is immobilized on the surface of the substrate. Also, the present invention provides a method for producing the substrate of the above-described present invention, the method comprising irradiating the substrate whose surface at least is composed of carbon with ultraviolet light during the acrylic polymer contacts the carbon. Further, the present invention provides a method for producing a biochip, the method comprising a step of preparing a substrate for biochips of the above-described present invention; and a step of binding a biologically relevant substance(s) to the free carboxyl groups.

Effect of the Invention

By the present invention, a substrate for biochips, whose surface is composed of carbon and has free carboxyl groups; and a method for producing the same are provided. Since the substrate for biochips of the present invention has the surface composed of carbon, the substrate for biochips has excellent properties that autofluorescence is not induced, processing of the substrate is easy, and high flatness and surface precision can be attained, and has free carboxyl groups on the surface.

MODE FOR CARRYING OUT THE INVENTION

The substrate for biochips of the present invention (hereinafter also referred to as simply "substrate" for short) is characterized in that an acrylic polymer is immobilized on the surface of the substrate. From the facts that acrylic acid or methacrylic acid is immobilized on carbon by irradiation with ultraviolet light as described below, and that the acrylic polymer is not eliminated even when washed while moving the substrate as concretely described in Examples below, the acrylic polymer is thought to be covalently bound to the carbon.

Among the acrylic polymers, polyacrylic acid, polymethacrylic acid or a copolymer comprising acrylic acid or methacrylic acid is preferred, and in particular, polyacrylic acid is more preferred. In cases where the acrylic polymer is a copolymer, components other than acrylic acid and methacrylic acid for a copolymer are not limited, and examples thereof include poly(acrylic acid-co-styrene), poly(acrylic acid-co-methacrylic acid) and poly(acrylic acid-co-ethylene). The copolymer may be any one of random copolymers, block copolymers and graft copolymers. The content of acrylic acid component or methacrylic acid component in the copolymer is usually 20 to 99%, preferably about 50 to 99% by mole. The average molecular weight (on a weight basis) of the acrylic polymer is not limited, and the average molecular weight is preferably 1000 or more, and more preferably 2000 or more from the viewpoint of better attaining the effect of the present invention. On the other hand, the upper limit of the molecular weight of the acrylic polymer is not limited as long as handlings such as solubility and stability of the coating solution are not problematic, and preferably 60,000 or less, more preferably 6,000 or less.

In the substrate for biochips of the present invention, at least the surface of the substrate is composed of carbon. As the carbon, amorphous carbon or diamond-like carbon is preferred. In order to promote the accuracy of measurement when used as a biochip, the surface of the substrate is preferably as flat as possible and may be polished as required. The surface roughness Ra is preferably 2 nm or less and more preferably about 1 nm.

The material of the substrate body is not limited in any way as long as at least the surface of the substrate is formed by carbon. The whole substrate can be constituted by carbon such as amorphous carbon; or diamond carbon or the like can be coated on the substrate body. The substrate body can be formed by any one of carbon, metal, glass, ceramics and plastic, or can be formed by a complex thereof. When carbon is not employed, the acrylic polymer may be immobilized on the surface after the treatment of providing a carbon layer on the surface thereof. Among these methods, a method of forming the whole substrate with carbon is particularly preferred in view of chemical resistance, heat resistance, and absence of auto-luminescence. As the metal, those wherein a carbon or diamond-like carbon layer is provided on the surface of aluminum, stainless steel, iron and steel, copper or the like, or alloy thereof by a treatment method such as spattering, CVD, PVD or the like in order to ensure a covalent bond with the polymer may be employed as the substrate material. Aluminum on the surface of which a surface treatment such as nickel-phosphate plating is applied in order to improve corrosion resistance and surface rigidity and then the above-described carbon layer is provided may be employed as the substrate material. Glass and ceramics are materials generally employed as a material for biochip substrates. A layer of carbon or diamond-like carbon may be further provided on the surface of the material by a treatment method such as spattering, CVD or PVD for the purpose of ensuring covalent bonds with the polymer, and for the purpose of preventing excess adsorption of protein test samples.

The acrylic polymer may be immobilized on carbon by applying the acrylic polymer solution on the carbon, drying the resulting substrate and irradiating the substrate with ultraviolet light. The solvent of the acrylic polymer solution is not limited as long as it can dissolve the acrylic polymer, and the solvent is preferably a polar solvent in view of solubility, and among these, ethanol and water is preferable in view of ease of handling. The concentration of the acrylic polymer in the solution is not limited, and is preferably about 0.5 to 3% (w/v). For the application of the acrylic polymer on the surface of the substrate, a general method may be employed and the method is not particularly limited as long as the method is the one in which the coating amount of the acrylic polymer can be controlled. For example, the method may be selected from roll coating, spray coating, spin coating, dip coating and the like and carried out.

As the ultraviolet light to be irradiated, ultraviolet rays having a wavelength of about 150 nm to 260 nm, for example, a wavelength of 184 nm or 254 nm may be employed. By the light having such a wavelength, the C—C, C—O and C—H bonds are cleaved to generate radicals. At this time, oxygen molecules and water molecules in the air are also decomposed to generate oxygen radicals and ozone, and at the same time, oxidative destruction of the substrate material carbon and polymer occurs, which causes inhibition of covalent bond formation. In order to prevent this, in the production method of the present invention, light irradiation is preferably performed under reduced pressure or under an inert gas atmosphere. The vacuuming may be performed at a degree of vacuum of −0.05 MPa or less, preferably −0.08 MPa or less based on atmosphere pressure (0 MPa). As an inert gas, a rare gas element such as argon or helium is employed which is hard to generate radicals even when a light is irradiated. Light dose may be any amount as long as the amount is the one which is needed for the polymer to be bound covalently, and is usually about 1 to 6 joules, preferably about 2 to 4 joules per 1 $cm^2$ of the surface of the substrate in terms of energy amount. For example, an ultraviolet ray of 18.5 mW per 1 $cm^2$ of the surface of the substrate is irradiated usually for 1 to 5 minutes, and preferably for 2 to 4 minutes. After the irradiation, the substrate is washed, and it is preferable to further carry out blocking with a commercially available blocking agent by a conventional method in order to prevent non-specific adsorption.

The thus obtained substrate of the present invention has carboxyl groups on the surface thereof uniformly and at a high density. By employing these carboxyl groups, a biologically relevant substance(s) is(are) immobilized by covalent bonds, thereby constituting biochips. The biologically relevant substance(s) may be any substance(s) which is(are) employed as probes on biochips, and examples thereof include any polypeptides (including natural or synthesized proteins and oligopeptides), nucleic acids (including DNAs and RNAs and artificial nucleic acids), sugars, lipids, complexes thereof (e.g., sugar proteins) and derivatives thereof (e.g., modified proteins or nucleic acids).

The biologically relevant substance(s) may be bound to the carboxyl groups easily by binding amino groups in the biologically relevant substance(s) and the carboxyl groups with amide bonds. In cases where the amino groups do not exist at desired sites (e.g. at the terminal and the like) in the biologically relevant substance(s), the amino groups may be given to desired sites by a conventional method using aminating agents. The amide bond may be easily formed, for example, according to a conventional method by using a condensing agent or the like.

The present invention will now be described more concretely by way of Examples. However, the present invention is not restricted to the Examples.

Example 1

1. Preparation of Substrate for Biochips
(1) Preparation of Substrate whose Surface is Carbon Using, as a substrate material, an amorphous carbon plate (25.0×75.0 mm, tolerance±0.1 mm, plate thickness 1.000 mm, tolerance±0.025 mm) which was polished such that the surface roughness Ra was 1 nm, a 15-minute ultraviolet irradiation (18.5 mW/$cm^2$, 254 nm) was performed by an ultraviolet irradiation apparatus (SEN LIGHTS Co., Ltd., Photo Surface Processor PL 16-110).
(2) Immobilization of Polyacrylic Acid Polyacrylic acid having a weight-average molecular weight of 5,000 was dissolved in ethanol at a concentration of 2 w/v %. The carbon surface of the above-described substrate was coated with the obtained polyacrylic acid solution. That is, a suitable amount of the coating solution was aliquoted with a pipette and dropped on the surface of the substrate material, and the coating solution was spread over the entire surface of the substrate material with a Baker applicator whose coating thickness was set at 2 mil (about 0.051 mm) so as to attain a coating amount of polyacrylic acid of 20 μg/cm². After volatilization of the solvent, the substrate was dried under vacuum (degree of vacuum: −0.098 MPa) for one hour, and then still under vacuum, a 4-minute ultraviolet irradiation (18.5 mW/cm², 254 nm) was performed to immobilize polyacrylic acid. Further, the substrate was stirred with ultrapure water for one hour to wash unreacted polyacrylic acid away and then subjected to spin drying to obtain a substrate for biochips of the present invention.

Example 2 Immobilization of Terminal-Aminated DNA and Performance

Evaluation
(1) Immobilization of Terminal-Aminated DNA and Blocking

PBS was added to a terminal-aminated DNA having a length of 50 base pairs, which was purchased from RIKAKEN, to a concentration of 10 nM. After spotting the 10 μM aqueous solution of the terminal-aminated DNA, the substrate was placed in a hybridization chamber, and 100 μL of pure water was added to each groove at the both sides of the the hybridization chamber, followed by closing the lid and sealing the chamber. The hybridization chamber was placed in humidistat at 95% RH, and incubation was performed for 5 hours. The removed substrate was dried in the air.

A commercially available blocking agent (10× blocking agent, produced by Agilent) was dissolved in 0.5 μL of pure water to prepare 10× blocking solution, and the prepared blocking solution was further diluted 10-fold to prepare 1× blocking solution. The substrate was placed in the hybridization chamber and a coverslip having a 20 nm gap was placed on the substrate such that the spot was covered, and 30 μL of 1× blocking solution was poured into the substrate from the gap. To each groove at the both sides of the the hybridization chamber, 100 μL of pure water was added, and after sealing the hybridization chamber, the substrate was left to stand at room temperature for 30 minutes. The substrate was washed while stirring with pure water for 5 minutes and then immersed in ethanol at 4° C. for 5 minutes, followed by spin-drying the substrate.
(2) Hybridization A hybridization solution was prepared by dissolving 3.09 μL of 100 μM Cy3-labeled DNA (complementary strand of immobilized DNA), 33 μL of 10× blocking solution and 165 μL of hybridization buffer in 128.9 μL of pure water. The substrate was placed in the hybridization chamber and a coverslip having a 20 μm gap was placed on the substrate such that the probe spot was covered, and 30 μL of hybridization solution was poured into the substrate from the gap. To each groove at the both sides of the the hybridization chamber, 100 μL of pure water was added, and the hybridization chamber was sealed and then put into an aluminum-laminated bag, thereby keeping the chamber in the dark. The hybridization was carried out in a dryer at 65° C. overnight. After taking out the hybridization chamber from the dryer, the substrate was immediately washed while moving using a slide washer with 2×SSC, 0.1 wt % SDS for 5 minutes. Since the coverslip is removed in the early stage of washing, the coverslip was moved to different grooves in a holder, and the washing of the coverslip was continued along with the substrate. The washing was performed with 0.2×SSC, 0.1 wt % of SDS for 5 minutes, then with 0.2×SSC for 5 minutes, and rinse was performed with pure water for 5 minutes, followed by spin drying.
(3) Measurement of Fluorescence Intensity The whole surface of the substrate was scanned by employing an excitation light of 532 nm, fluorescence filter of 570 nm, resolution of 10 μm and PMT of 50%.
(4) Results The results are shown in Table 1 below. In the Table, "PAc" means polyacrylic acid, "U4" means ultraviolet irradiation for 4 minutes, "LAU" means linear arbitrary unit, "SN" means signal-noise ratio and "BG" means background (fluorescence of DNA-unimmobilized site).

TABLE 1

| PAc 2% U4 DNA immobilized | LAU/mm² | SN |
|---|---|---|
| 1 | 463 | 4.2 |
| 2 | 565 | 5.1 |
| 3 | 637 | 5.7 |
| 4 | 388 | 3.5 |
| 5 | 416 | 3.7 |
| 6 | 514 | 4.6 |
| 7 | 263 | 2.4 |
| 8 | 311 | 2.8 |
| 9 | 387 | 3.5 |
| BG | 111 | — |

As shown in Table 1, SN ratio is 3.9 on average, and it was proved that the complementary strand of the immobilized DNA can be detected by using the biochips having DNA immobilized on the substrate for biochips of the present invention.

The invention claimed is:

1. A method for producing a substrate for biochips, said method comprising:
   irradiating a substrate whose surface at least is composed of amorphous carbon with ultraviolet light while an acrylic polymer having free carboxyl groups in the molecular structure thereof contacts said substrate,
   wherein said acrylic polymer has an average molecular weight of 2,000 to 100,000,
   wherein said acrylic polymer is selected from the group consisting of polyacrylic acid, polymethacrylic acid, and a copolymer of acrylic acid and methacrylic acid, and
   wherein the acrylic polymer becomes immobilized directly on the surface of said substrate.

2. The method according to claim 1, wherein said acrylic polymer is polyacrylic acid.

3. A method for producing a biochip, said method comprising
   preparing the substrate for biochips according to claim 1; and
   binding a biologically relevant substance(s) to said free carboxyl groups.

4. The method according to claim 3, wherein said biologically relevant substance(s) is(are) at least one selected from the group consisting of polypeptides, nucleic acids, sugars, lipids and complexes thereof.

* * * * *